United States Patent
Shimomura et al.

(10) Patent No.: US 12,414,963 B2
(45) Date of Patent: *Sep. 16, 2025

(54) TREATMENT OF SLEEP-WAKE DISORDERS AND NEURODEGENERATIVE DISEASE COMPRISING MODIFIED RESISTANT MALTODEXTRIN

(71) Applicant: Northwestern University, Evanston, IL (US)

(72) Inventors: Kazuhiro Shimomura, Wilmette, IL (US); Martha Hotz Vitaterna, Northbrook, IL (US); Phyllis C. Zee, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/828,758

(22) Filed: May 31, 2022

(65) Prior Publication Data
US 2023/0017911 A1    Jan. 19, 2023

Related U.S. Application Data

(63) Continuation of application No. 16/191,166, filed on Nov. 14, 2018, now Pat. No. 11,344,569.

(60) Provisional application No. 62/585,921, filed on Nov. 14, 2017.

(51) Int. Cl.
*A61K 31/716* (2006.01)
*A61K 31/718* (2006.01)
*A61P 25/00* (2006.01)
*A61P 25/28* (2006.01)

(52) U.S. Cl.
CPC .......... *A61K 31/716* (2013.01); *A61K 31/718* (2013.01); *A61P 25/00* (2018.01); *A61P 25/28* (2018.01)

(58) Field of Classification Search
CPC ..... A61K 31/716; A61K 31/718; A61P 25/00; A61P 25/28
USPC ......................................................... 514/58
See application file for complete search history.

(56) References Cited

U.S. PATENT DOCUMENTS

| | | | |
|---|---|---|---|
| 7,053,084 B1 | 5/2006 | Olson | |
| 7,932,238 B2 | 4/2011 | Wils | |
| 8,871,740 B2 * | 10/2014 | Guerin-Deremaux | A61P 25/24 536/103 |

OTHER PUBLICATIONS

Prusiner, The New England Journal of Medicine, 2001, 344 (20), 1516-1526.*
Winquist et al, Biochemical Pharmacology, 2007, 74, 1321-1329.*
Davidson et al, New England Journal of Medicine, 2001, 345 (5), 340-350.*
Holmes et al, Epileptic Disord 2015, 17(2), 101-116.*
Landolt et al, Neurology, 2006, 66, 1418-1424.*
Caminero et al, Journal of Neurological Sciences, 2011, 309, 86-91.*
Mahesh et al, American Journal of Phytomedicine and Clinical Therapeutics, 2014, 2(4), 463-468.*
Pushpanathan et al, Sleep Medicine Reviews 2016, 26, 21-32.*
Akbari, et al., Effect of Probiotic Supplementation on Cognitive Function and Metabolic Status in Alzheimer's Disease: A Randomized, Double-Blind and Controlled Trial. Front Aging Neurosci. 2016;8:256. Epub Nov. 29, 2016. doi: 10.3389/fnagi.2016.00256. PubMed PMID: 27891089; PMCID: PMC5105117.
Baer, et al., The metabolizable energy of dietary resistant maltodextrin is variable and alters fecal microbiota composition in adult men. J Nutr. 2014;144(7):1023-9. doi: 10.3945/jn.113.185298. PubMed PMID: 24744316.
Brandscheid, et al., Altered Gut Microbiome Composition and Tryptic Activity of the 5xFAD Alzheimer's Mouse Model. J Alzheimers Dis. 2017;56(2):775-88. Epub Dec. 31, 2016. doi: 10.3233/JAD-160926. PubMed PMID: 28035935.
Cummings, Lessons Learned from Alzheimer Disease: Clinical Trials with Negative Outcomes. Clin Transl Sci. 2018;11(2):147-52. Epub Aug. 3, 2017. doi: 10.1111/cts.12491. PubMed PMID: 28767185; PMCID: PMC5866992.
Djonlagic, et al., Increased sleep fragmentation leads to impaired off-line consolidation of motor memories in humans. PLoS One. 2012;7(3):e34106. doi: 10.1371/journal.pone.0034106. PubMed PMID: 22470524; PMCID: PMC3314699.
Fastinger, et al., A novel resistant maltodextrin alters gastrointestinal tolerance factors, fecal characteristics, and fecal microbiota in healthy adult humans. J Am Coll Nutr. 2008;27(2):356-66. PubMed PMID: 18689571.
Gao, et al., Multiple classifier systems for automatic sleep scoring in mice. J Neurosci Methods. 2016;264:33-9. Epub Mar. 2, 2016. doi: 10.1016/j.jneumeth.2016.02.016. PubMed PMID: 26928255; PMCID: PMC4833589.
Hashizume, et al., Fiber Ingredients: Food Application and Health Benefits. CRC press. 2009:pp. 61-78.
Hashizume, et al., Improvement effect of resistant maltodextrin in humans with metabolic syndrome by continuous administration. J Nutr Sci Vitaminol (Tokyo). 2012;58(6):423-30. PubMed PMID: 23419401.
He, et al., Transmissible microbial and metabolomic remodeling by soluble dietary fiber improves metabolic homeostasis. Sci Rep. 2015;5:10604. doi: 10.1038/srep10604. PubMed PMID: 26040234; PMCID: PMC4455235.
Laposky, et al., Sleep-wake regulation is altered in leptin-resistant (db/db) genetically obese and diabetic mice. Am J Physiol Regul Integr Comp Physiol. 2008;295(6):R2059-66. doi: 10.1152/ajpregu. 00026.2008. PubMed PMID: 18843095; PMCID: PMC2685290.
Liberti, et al., The Warburg Effect: How Does it Benefit Cancer Cells? Trends Biochem Sci. 2016;41(3):211-8. Epub Jan. 19, 2016. doi: 10.1016/j.tibs.2015.12.001. PubMed PMID: 26778478; PMCID: PMC4783224.
Lim, et al., Sleep Fragmentation and the Risk of Incident Alzheimer's Disease and Cognitive Decline in Older Persons. Sleep. 2013;36(7):1027-32. doi: 10.5665/sleep.2802. PubMed PMID: 23814339; PMCID: PMC3669060.

(Continued)

*Primary Examiner* — Ganapathy Krishnan
(74) *Attorney, Agent, or Firm* — Quarles & Brady LLP

(57) ABSTRACT

The invention relates to compositions and methods of treating a sleep-wake disorder or neurodegenerative diseases using modified resistant maltodextrin.

9 Claims, 11 Drawing Sheets

(56) References Cited

OTHER PUBLICATIONS

Maqsood, et al., The Gut-Brain Axis, BDNF, NMDA and CNS Disorders. Neurochem Res. 2016;41(11):2819-35. doi: 10.1007/s11064-016-2039-1. PubMed PMID: 27553784.

Minter, et al., Antibiotic-induced perturbations in gut microbial diversity influences neuro-inflammation and amyloidosis in a murine model of Alzheimer's disease. Sci Rep. 2016;6:30028. Epub Jul. 23, 2016. doi: 10.1038/srep30028. PubMed PMID: 27443609; PMCID: PMC4956742.

Oakley, et al., Intraneuronal beta-amyloid aggregates, neurodegeneration, and neuron loss in transgenic mice with five familial Alzheimer's disease mutations: potential factors in amyloid plaque formation. J Neurosci. 2006;26(40):10129-40. Epub Oct. 6, 2006. doi: 10.1523/JNEUROSCI. 1202-06.2006. PubMed PMID: 17021169.

Sancho, et al., Fibersol-2 induces apoptosis of Apc-deficient colorectal Cancer (SW480) cells and decreases polyp formation in Apc MIN mice. Cancer Biol Ther. 2016;17(6):657-63. Epub May 5, 2016. doi: 10.1080/15384047.2016.1177685. PubMed PMID: 27143108; PMCID: PMC4990394.

Saulnier, et al., The intestinal microbiome, probiotics and prebiotics in neurogastroenterology. Gut Microbes. 2013;4(1):17-27. Epub Dec. 4, 2012. doi: 10.4161/gmic.22973. PubMed PMID: 23202796; PMCID: PMC3555881.

Sethi, et al., Increased fragmentation of sleep-wake cycles in the 5XFAD mouse model of Alzheimer's disease. Neuroscience. 2015;290:80-9. Epub Feb. 1, 2015. doi: 10.1016/j.neuroscience. 2015.01.035. PubMed PMID: 25637807; PMCID: PMC4361816.

So, et al., Tumor suppression by resistant maltodextrin, Fibersol-2. Cancer Biol Ther. 2015;16(3):460-5. Epub Feb. 19, 2015. doi: 10.1080/15384047.2015.1009269. PubMed PMID: 25692338; PMCID: PMC4622535.

Sochocka, et al., The Gut Microbiome Alterations and Inflammation-Driven Pathogenesis of Alzheimer's Disease—a Critical Review. Mol Neurobiol. 2018. Epub Jun. 25, 2018. doi: 10.1007/s12035-018-1188-4. PubMed PMID: 29936690.

Sprecher, et al., Poor sleep is associated with CSF biomarkers of amyloid pathology in cognitively normal adults. Neurology. 2017;89(5):445-53. doi: 10.1212/WVNL.0000000000004171. PubMed PMID: 28679595; PMCID: PMC5539733.

Tranah, et al., Circadian activity rhythms and risk of incident dementia and mild cognitive impairment in older women. Ann Neurol. 2011;70(5):722-32. Epub Dec. 14, 2011. doi: 10.1002/ana. 22468. PubMed PMID: 22162057; PMCID: PMC3244839.

Vogt, et al., Gut microbiome alterations in Alzheimer's disease. Sci Rep. 2017;7(1):13537. Epub Oct. 21, 2017. doi: 10.1038/s41598-017-13601-y. PubMed PMID: 29051531; PMCID: MC5648830.

Walsh, et al., Weaker circadian activity rhythms are associated with poorer executive function in older women. Sleep. 2014;37(12):2009-16. doi: 10.5665/sleep.4260. PubMed PMID: 25337947.

Winrow, et al., Uncovering the genetic landscape for multiple sleep-wake traits. PLoS One. 2009;4(4):e5161. Epub Apr. 11, 2009. doi: 10.1371/journal.pone.0005161. PubMed PMID: 19360106; PMCID: PMC2664962.

Davidson et al, Autoimmune Diseases, New England Journal of Medicine, 2001, vol. 345, No. 5, p. 340-350.

The Merck Manual of Diagnosis and Therapy, 16th Ed., 1999, pp. 339-342 and 1488-1490.

Beran et al., Interface of epilepsy and sleep disorders, Seizure, 1999; 8:97-102.

Hsiao et al., Sleep Disorders and Increased Risk of Autoimmune Diseases in Individuals without Sleep Apnea, Sleep, 2015; 38(e):581-586.

Ye, et al., Soluble dietary fiber (Fibersol-2) decreased hunger and increased satiety hormones in humans when ingested with a meal, Nutrition Research, vol. 35, No. 5, 2015, pp. 393-400.

ADM, Fibersol-2 Digestion Resistant Maltodextrin, Jan. 1, 2004, pp. 1-8, XP055339778.

Ohkuma, K., et al., Fibersol-2: a Soluble, Non-digestible, Starch-derived Dietary Fibre, Advanced Dietary Fibre Technology, Jan. 1, 2001, pp. 509-523.

International Search Report, corresponding to PCT/US2018/061071, Feb. 5, 2019, pp. 1-3.

* cited by examiner

FIG. 3B
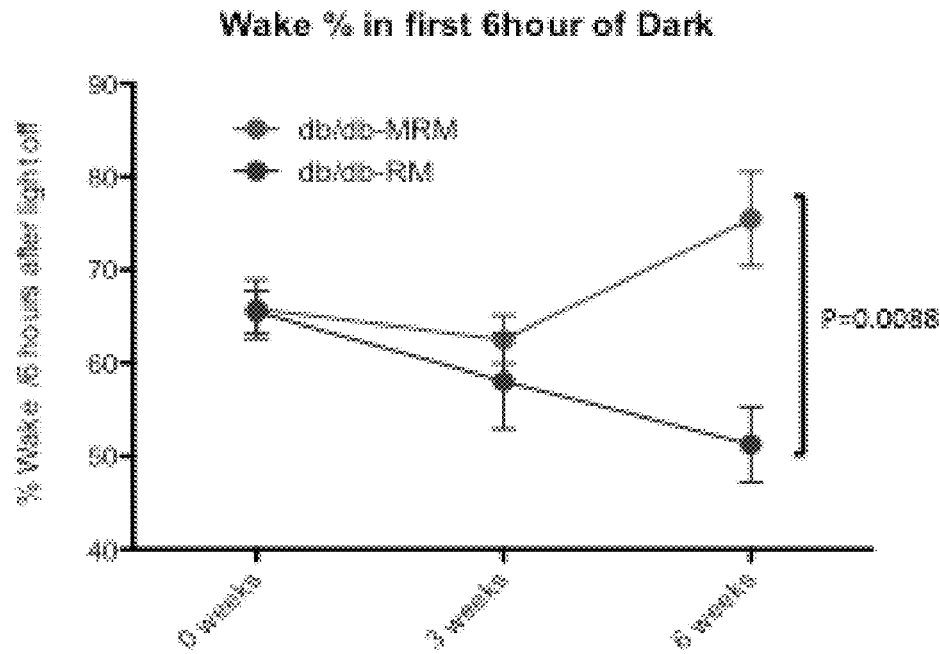
FIG. 3C
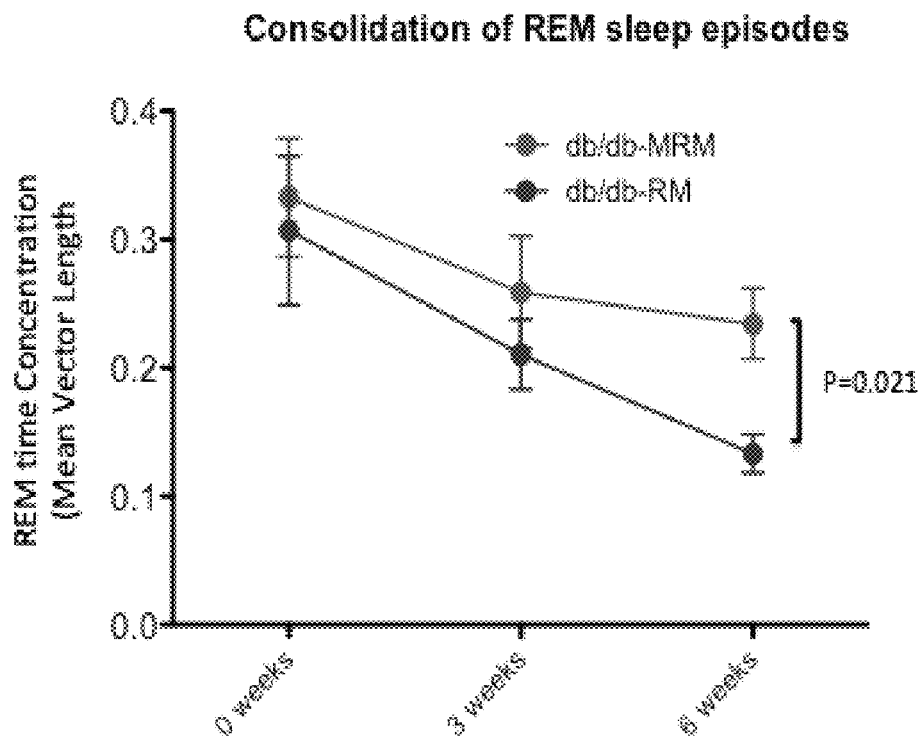
FIGS. 3A-3D (Continued)

A
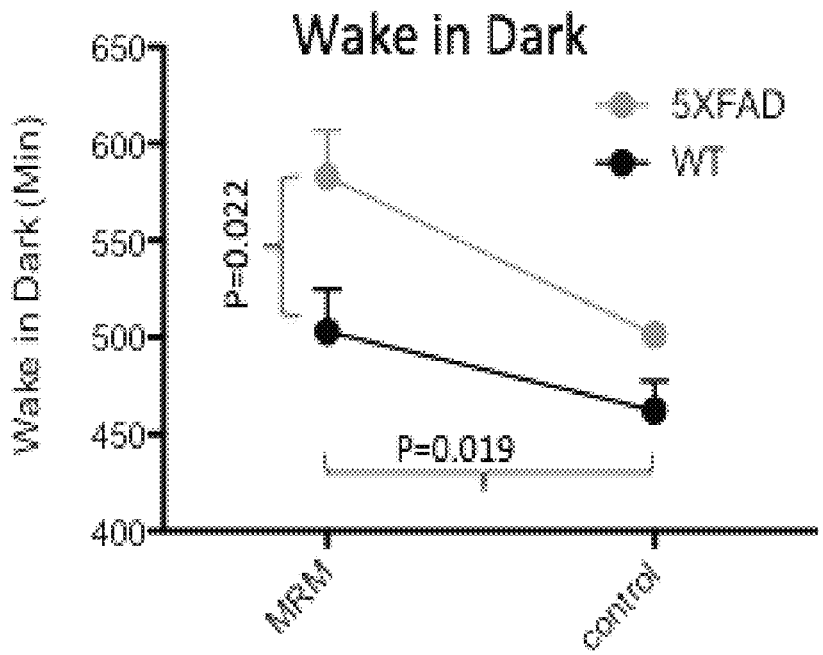
B
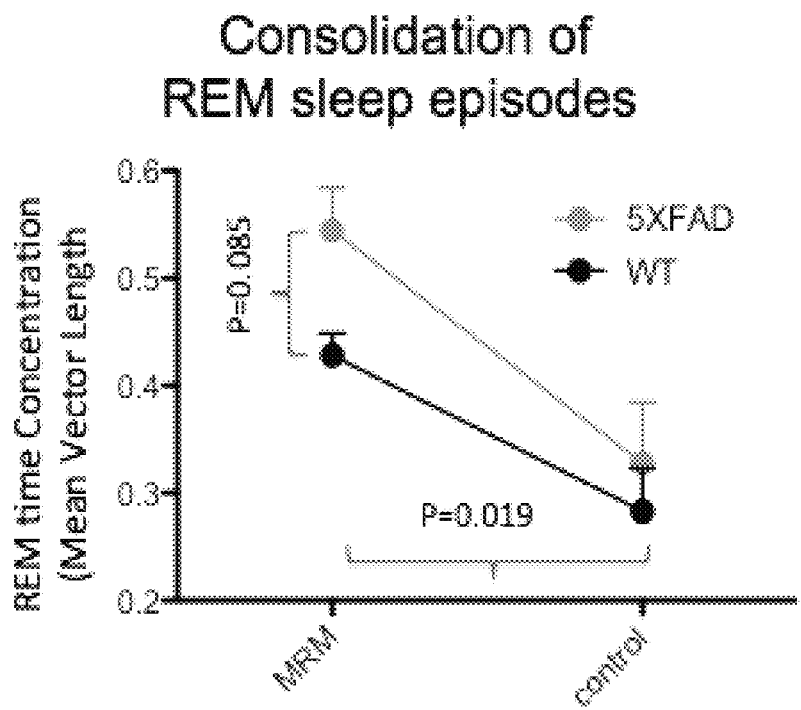
FIGS. 4A-B

A.
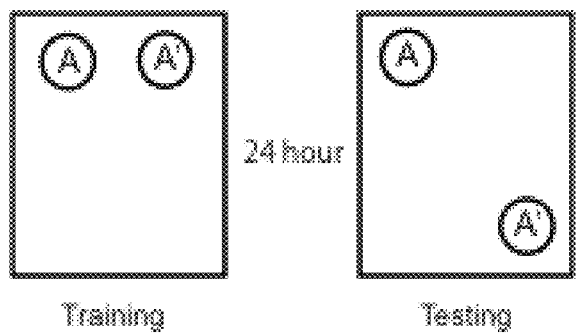
B.
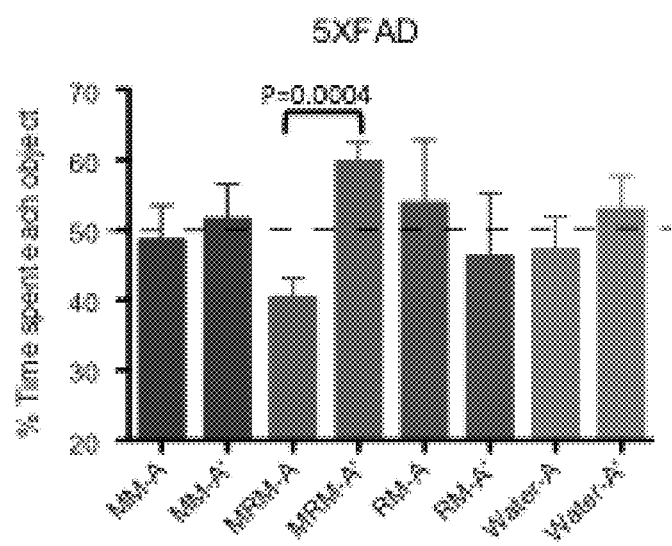
C.
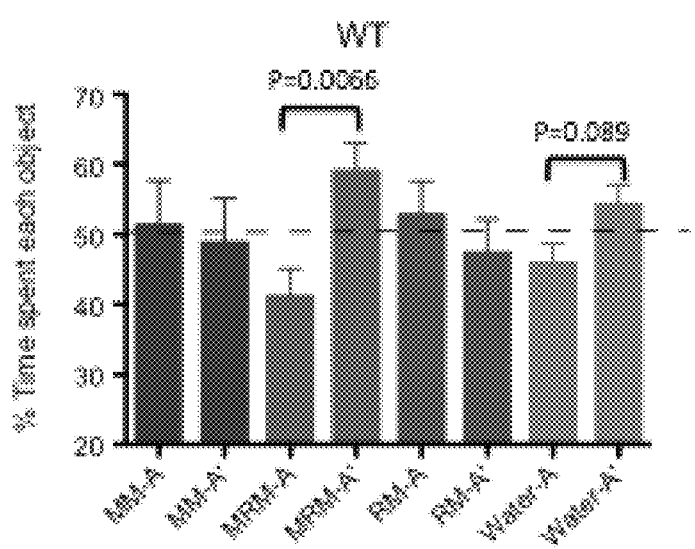
FIG. 5A-C

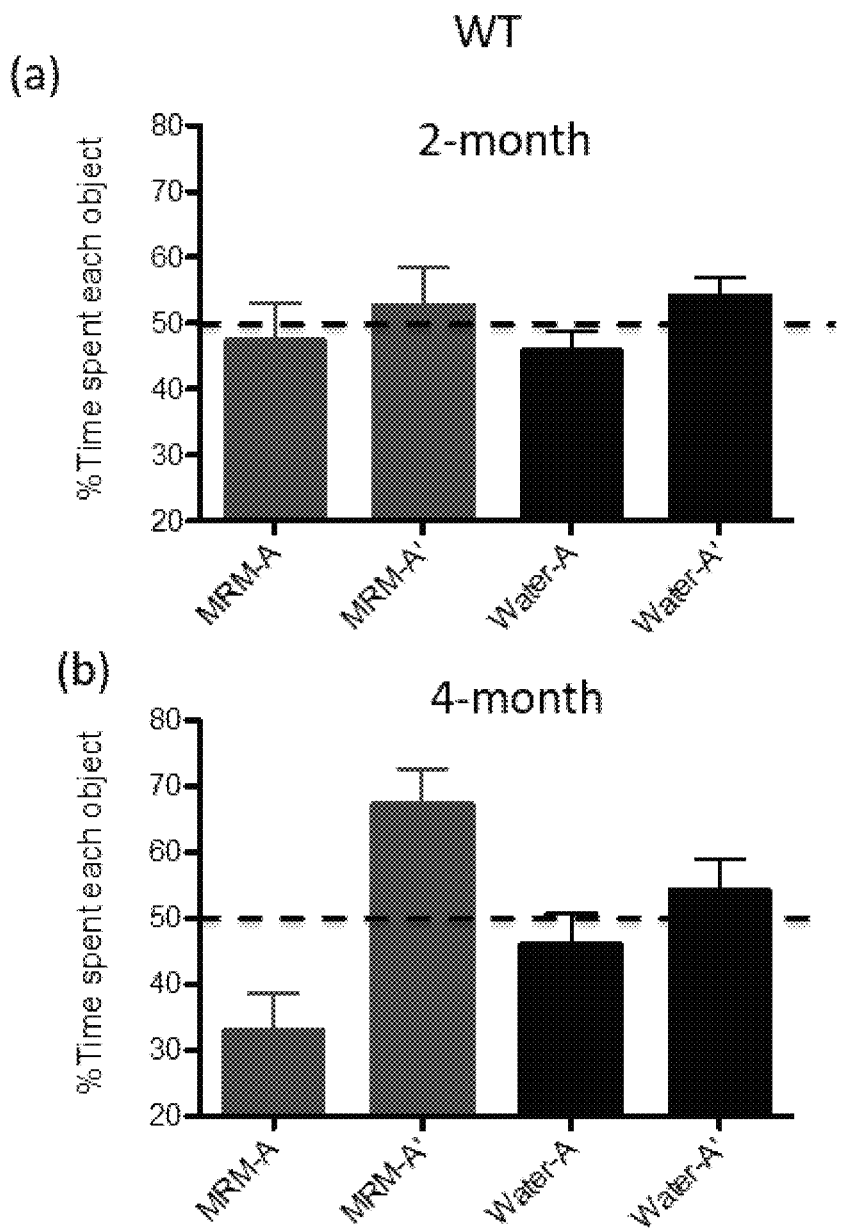
FIGS. 7A-D

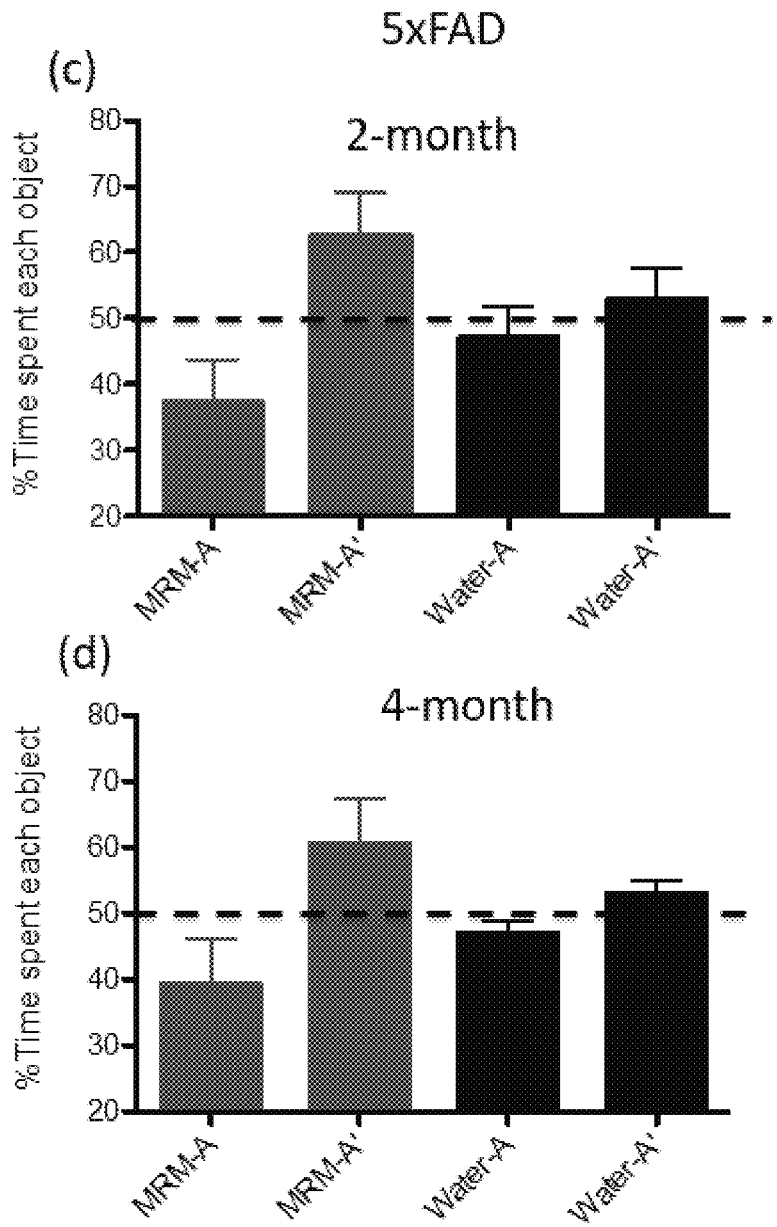
FIGS. 7A-D (continued)

TREATMENT OF SLEEP-WAKE DISORDERS AND NEURODEGENERATIVE DISEASE COMPRISING MODIFIED RESISTANT MALTODEXTRIN

CROSS-REFERENCE TO RELATED APPLICATIONS

This application claims priority to U.S. Provisional Application No. 62/585,921 filed on Nov. 14, 2017, the contents of which are incorporated by reference in its entirety.

STATEMENT REGARDING FEDERALLY SPONSORED RESEARCH

N/A

BACKGROUND OF THE INVENTION

The field of the invention is related to therapeutics and methods of treating sleep-wake disorders and neurodegenerative disease.

Sleep disturbances affect more than 25 percent of the general population and as many as 50 percent of older adults. The sleep of older adults is characterized by frequent arousals from sleep, reduced sleep quality and increased sleep fragmentation. Reduced sleep quality are both hallmarks of, and risk factors for, cardiometabolic disease and other age-related conditions such as neurodegenerative diseases.

Disruptions of the circadian timing of sleep, such as increased daytime sleepiness, are also associated with many of the same diseases. Although available hypnotics and sleep aids may increase sleep time or reduce sleep latency, they do not specifically address these sleep disorders seen in the populations including age-associated cardiometablic disorders and neurodegenerative diseases.

As world populations age, it is crucial to develop safe and cost-effective therapeutics to improve sleep quality. As of 2014, North America accounted for the largest share of the gerontology/aging healthcare market, followed by Europe. The median age of the U.S. population has increased by almost 2 years per decade from 1970 to 2016. In addition to the need for sleep therapies, the market for preventive medicines or anti-aging nutritional supplements is growing along with the aging population.

Alzheimer's disease (AD) is the most prevalent neurodegenerative disease affecting 5 million Americans and ~30 million people world-wide. Many therapies developed to treat AD, including small molecule drugs or immune therapies, have focused on blocking the actions of key disease-causing proteins in the brain such as Aβ and tau. Most of the large clinical trials designed to test therapies that reduce the expression of Aβ have failed to show efficacy, and limited information is available regarding clinical trials testing those therapies targeting tau. At present no therapy has been shown to slow the progression of AD(2).

Because neurodegeneration in brain parallels AD progression and the toxic actions of Aβ and tau are most prominent in brain, most drug discovery and development programs have focused on therapeutics that target the brain to treat AD. This has involved either small molecule drugs that enter brain to block secretases involved in Aβ production or blocking kinases involved in tau phosphorylation, or immune related therapies that reduce Aβ or tau in the central nervous system (CNS).

There is a need for new therapeutic agents for the treatment of sleep-wake disorders and neurodegenerative disease.

SUMMARY OF THE INVENTION

The present disclosure overcomes the aforementioned drawbacks by providing methods of treating sleep-wake disorders, including neurodegenerative diseases, such as Alzheimer's disease.

In one aspect, the disclosure provides a method of treating a sleep-wake disorder in a subject in need thereof, the method comprising administering an effective amount of modified resistant maltodextrin to treat the sleep-wake disorder.

In another aspect, the disclosure provides a method of improving sleep quality in a patient in need thereof, the method comprising administering an effective amount of modified resistant maltodextrin to improve sleep quality in the patient.

In yet a further aspect, the disclosure provides a method of reducing symptoms of sleep disorders associated with aging, cardiometabolic disorder, or neurological disorder in a subject, the method comprising administering an effective amount of modified resistant maltodextrin to reduce symptoms of the sleep disorder in the subject.

In another aspect, the disclosure provides a method of treating Alzheimer's disease in a subject, the method comprising administering an effective amount of modified resistant maltodextrin to treat Alzheimer's disease.

In a further aspect, the disclosure provides a composition comprising modified resistant maltodextrin. In some aspects, the composition further comprises a pharmaceutically acceptable carrier.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

FIG. 3A depicts the time spent awake during the first six hours of the dark period for mice that were treated with the RM (blue) and MRM (red). Mitigation of excessive nighttime sleepiness (3B), concentration of REM sleep episodes to the correct time (3C) and fragmentation of sleep (3D) is shown for db/db mice by MRM. db/db mice consumed either 1% MRM or RM for 6 weeks during which contiguous sleep recording was conducted. Values are presented as means±SEM of 4-6 mice. P-values shown are result of t-test after 6 weeks between MRM or RM treatment.

FIGS. 4A-B demonstrate mitigation of excessive night time sleepiness (A) and consolidation of REM sleep episodes (B) in 5×FAD and WT mice by MRM. Mice consumed either 1% MRM or control (modified maltodextrin, MM) for 4 months starting at 2 months of age. Sleep recording was conducted after 4 months of feeding. Values are presented as means±SEM of 2-4 mice. P-values shown are the result of Two-way ANOVA. (MM control was created from maltodextrin with identical method to create MRM.)

FIGS. 5A-C shows improvement of memory consolidation in 5×FAD and WT mice treated with 1% MRM for 4 months compared to treatment with MM, RM and water for 4 months. Schematic diagram of object location memory test is shown in (A). Specifically, after 2 hours of acclimation, we allow mice to explore two identical objects for 5 minutes followed by a 10-minute inter-trial. After 2nd 5 min training, mice were moved to their home cage. 24 hours later, mice were placed in the same testing chamber. After 2 hours of acclimation, we moved one of the objects to a new location (A') and allowed animals to explore for 5 minutes. The percent of time explored for each object is quantified for 5×FAD (B) and WT (C). Values are presented as means±SEM of 4-11 mice. P-values shown are result of Student t-test between preference for object A and A' in each treatment and genotype.

FIGS. 7A-D demonstrates that fecal microbiota from MRM raised mice confer improvement of memory consolidation of MRM in recipient mice. Recipient mice (5×FAD or WT) were first treated with antibiotics cocktail to remove a vast majority of intrinsic gut bacteria. Subsequently, fecal suspensions from MRM treated donor mice (4 month treatment, 4 WT and 4 5×FAD) were pooled and administered to respective recipient mice via oral gavage. Object location memory tests were conducted 2 and 4 months after fecal microbiota transplantation (FMT). After 2 month of FMT, only 5×FAD mice showed significant improvement of memory consolidation compared to control mice without FMT (FIG. 7 A, C). After 4 month of FMT, we observed memory improvement in both WT and 5×FAD (FIG. 7 B, D). Of note, the recipient mice were never exposed to MRM indicating that gut microbiota in MRM donors were sufficient to confer the efficacy of MRM in memory consolidation after 24 hours in recipient mice.

DETAILED DESCRIPTION OF THE INVENTION

Figure 1A:
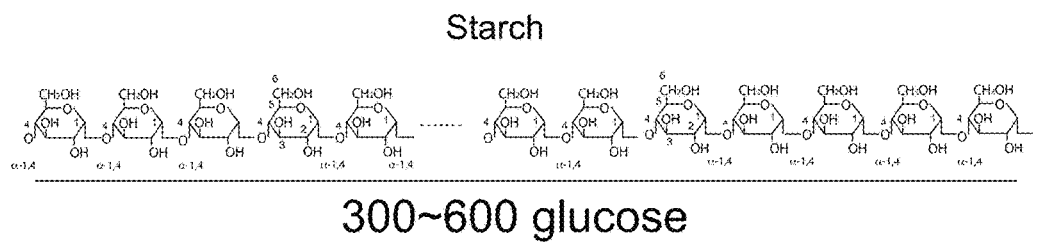
FIG. 1A depicts the structure of starch. Starch is a polymeric carbohydrate consisting of a large number of glucose units (300-600) joined by mainly glucosidic alpha1-4 bonds.

The present invention provides methods of treating sleep-wake disorders including Alzheimer's disease.

Specifically, in one embodiment, the present invention provides methods of treating sleep disorders common to aging, cardiometabolic disease, and neurodegenerative disorders. These chronic conditions and patient populations are not amenable to treatment by conventional hypnotic compounds. Available hypnotics are not suited to long-term use, do not address all aspects of the sleep disorders prevalent in these populations, and may have undesirable or dangerous side effects in patients suffering from these conditions. The modified resistant maltodextrin used in embodiments of the present invention is believed to be safe and well-tolerated in all of these populations, and able to mitigate multiple sleep disturbances common to these populations.

The inventors have modified commercially available resistant maltodextrin using heat as described in the example. The provided modified version of the resistant maltodextrin surprisingly and unexpectedly significantly improves sleep quality by reducing sleep fragmentation, and increasing circadian amplitude and REM sleep consolidation in db/db mouse.

One embodiment provides a method of treating a sleep-wake disorder in a subject in need thereof, the method comprising administering an effective amount of modified resistant maltodextrin (MRM) to treat the sleep-wake disorder.

The terms "subject" and "patient" are used interchangeably and refer to any animal (e.g., a mammal), including, but not limited to, humans, non-human primates, rodents, and the like, which is the recipient of a particular treatment. Typically, the terms "subject" and "patient" are used interchangeably herein in reference to a human subject. In a preferred embodiment, the subject is a human having a sleep-wake disorder, preferably a sleep-wake disorder related to aging, cardiometabolic disease, or a neurodegenerative disease. In one embodiment, the subject is a human having or suspected of having a neurological disease, for example, a human having or suspected of having Alzheimer's disease.

The term "treat," "treating" or "treatment" of a sleep-wake disorder encompasses, but is not limited to, reducing, inhibiting or limiting the symptoms of a sleep-wake disorder. In some embodiments, the term treating encompasses reducing excessive daytime sleepiness, nocturnal restlessness or a combination thereof. In some embodiments, treating encompasses improving one or more of the following symptoms that is associated with one or more sleep-wake disorder: difficulty falling or staying asleep, sleep fragmentation (arousals and awakening after sleep onset), impaired daytime function (concentration, mood and cognition) or a combination thereof.

Suitable sleep wake disorders that can be treated by the methods described herein are those in which improvement in sleep duration, slow wave sleep and sleep continuity are treatment targets, which include, but are not limited to, for example, an insomnia disorder, hypersomnolence disorder and circadian rhythm sleep-wake disorders, or a sleep disorder associated with a medical condition.

Embodiments of the disclosure also provide a method of improving sleep quality in a patient in need thereof, the method comprising administering an effective amount of modified resistant maltodextrin to improve sleep quality in the patient. Improvement of sleep quality can be seen by improving one or more symptom of poor sleep quality, for example, reducing sleep fragmentation, increasing circadian amplitude, increasing REM sleep consolidation, or a combination thereof.

Embodiments of the disclosure also provide methods of reducing at least one symptom of a sleep disorder associated with aging, cardiometabolic disorder, or neurological disorder in a subject. Suitable methods comprise administering an effective amount of modified resistant maltodextrin to reduce at least one symptom of the sleep disorder in the subject.

In some embodiments, the treatment results in the improvement of the circadian timing of the sleep-wake cycle of the subject. In some preferred embodiments, the subject suffers from a cardiometabolic disorder or a neurological disorder.

Cardiometabolic syndrome (CMS) or cardiometabolic disorder is a disorder characterized by a combination of metabolic dysfunctions including, for example, insulin resistance, impaired glucose tolerance, dyslipidemia, hypertension, and central adiposity. CMS is recognized as a disease entity by the World Health Organization and the American Society of Endocrinology. In many instances, cardiometabolic disorder is associated with a sleep-wake disorder and can be associated with one or more symptoms associated with a sleep-wake disorder.

In another embodiment, the methods treat a sleep-wake disorder or sleep disorder associated with a neurological disease. Suitable neurological diseases in which a symptom is a sleep-wake disorder include, but are not limited to, age and neurodevelopmental conditions, for example, Alzheimer's disease, Parkinson's disease, and autism spectrum disorders. In a preferred embodiment, the neurological disease is Alzheimer's disease.

In some embodiments, the present disclosure provides methods of treating a neurological disease associated with sleep-wake disorder, including, but not limited to, Alzheimer's disease, Parkinson's disease, autism, multiple sclerosis, among others. Preferably, in one embodiment, the neurological disease is Alzheimer's disease. The method comprises administering a therapeutically effective amount to treat the neurological disease.

In some embodiments, the present disclosure provides methods of treating immune disorders associated with sleep-wake disorders. Not to be bound by any theory, but some immune and autoimmune disorders may be considered as having an etiology stemming from disturbed sleep. There is evidence that there is a complex interaction between the immune system and the sleep-wake cycle, which is involved in regulating normal immune function. The present disclosure contemplates the treatment of immune disorders, including, but not limited to, asthma, eczema, irritable bowel syndrome, fibromyalgia, chronic fatigue syndrome, systemic lupus erythematosus (SLE), myasthenia gravis, multiple sclerosis (MS), rheumatoid arthritis (RA), and other arthritic syndromes, among others. The method comprises administering a therapeutically effective amount to treat the immune disorder.

The term "treat," "treating" or "treatment" of a neurological disease encompasses, but is not limited to, reducing, inhibiting or limiting the symptoms of the neurological disease. In some embodiments, the term treating encompasses reducing symptoms of the neurological disease, for example, but not limited to, excessive daytime sleepiness, confusion, dementia, poor cognitive abilities, decreased alertness, memory loss, nocturnal restlessness, impaired daytime function (concentration, mood and cognition), or a combination thereof.

When the neurological disease is Alzheimer's, treating, treat or treatment includes, but is not limited to, reducing, inhibiting or limiting the symptoms of Alzheimer's disease. Symptoms of Alzheimer's disease, include, but are not limited to, for example, memory loss, difficulty planning, difficulty solving problems, difficulty completing familiar tasks, difficulty determining time or place, vision loss, difficulty finding the right words, forgetfulness, misplacing items often, difficulty making decisions, symptoms of dementia, withdrawing from work or social events, personality or mood changes, among others.

In some embodiments, the methods and compositions are used to treat Alzheimer's disease in an older adult, for example, an adult over the age of 55, preferably an adult over the age 65. In other examples, the methods and compositions are used to treat Alzheimer's disease in a patient diagnosed or suspected of having Alzheimer's disease.

In another embodiment, the methods are used to treat sleep-wake disorders in an older adult. In one embodiment, the method improves the circadian timing of the sleep-wake cycle in the older adult. An older adult may include a person over the age of 55, preferably over the age of 65.

The term "effective amount" or "therapeutically effective amount" refer to an amount sufficient to effect beneficial or desirable biological and/or clinical results. In one embodiment, the "effective amount" is an amount sufficient to reduce, inhibit or improve one or more symptom associated with the sleep-wake disorder and/or neurological disease.

The modified resistant maltodextrin can be administered in suitable form for oral administration. Suitable forms include, but are not limited to, a liquid, a solid (e.g. a capsule, tablet, lozenge, cachet, etc.)

The present disclosure also provides modified resistant maltodextrin and compositions comprising the modified resistant maltodextrin. Modified resistant maltodextrin can be prepared by heating Resistant Maltodextrin (www.fibersol.com/products/fibersol-2/) at from 95° C.-160° C., preferably about 120° C.-160° C. (e.g., 140° C.) for 20-60 minutes producing modified resistant maltodextrin. Another suitable embodiment for preparing MRM is by heating resistant maltodextrin at about 95° C.-120° C. overnight, preferably about 95° C. overnight (e.g., from 8-16 hours).

In another suitable embodiment, the modified resistant maltodextrin can be produced from starch by first treating starch with amylase and glucoamylase for a sufficient time to produce resistant maltodextrin which can then be prepared as described above into modified resistant maltodextrin.

The present disclosure also provides compositions for treating a sleep-wake disorder or neurological disorders, including Alzheimer's, the compositions comprising the modified resistant maltodextrin described herein in a pharmaceutically acceptable carrier.

In some embodiments, the modified resistant maltodextrin is made in a suitable composition for the route of administration. Suitable compositions may also include a pharmaceutically acceptable carrier.

The term "pharmaceutically acceptable carrier" refers any carrier, diluent or excipient that is compatible with the other ingredients of the formulation and not deleterious to the recipient. A pharmaceutically acceptable carrier can be selected on the basis of the selected route of administration and standard pharmaceutical practice. The MRM may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa, which is incorporated by reference in its entirety. Suitable dosage forms may comprise, but are not limited to, for example, solutions, parenteral solutions, injectable solutions, troches, suppositories, or suspensions.

The pharmaceutical composition is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials, or ampoules. Also, the unit dosage form can be a capsule, tablet, cachet, or lozenge itself, or it can be the appropriate number of any of these in packaged form.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents, and the like.

Another oral administration may be the formation of a liquid or gel suitable for oral dosage. In one embodiment, the MRM may be formulated in water, juice, or other beverage for oral consumption.

Suitable dosages of the modified resistant maltodextrin used in the present methods includes amounts of about 10 g/day to about 100 g/day, preferably about 30 g/day. For example, a suitable dosage may be 10 g/meal, or 3 times a day.

The compositions and methods described herein may be used to improve the quality of sleep and wakefulness. In some embodiments, the methods increase the amount of sleep for an individual, or decrease the amount of restlessness or non-sleep time during a sleep period of time.

The composition and methods described herein may be use to improve memory and/or cognition in a subject having a neurological disease, preferably Alzheimer's disease.

The modified resistant maltodextrin is believed to be relatively safe and tolerated for long-term use, because the original material used is dietary oligosaccharide.

The modified resistant maltodextrin may be used for the treatment of Alzheimer's disease. The compositions and methods of the present disclosure are significant because we are employing an entirely different approach to treat AD by developing therapeutic compositions that act in the gut to affect the microbiome.

Not to be bound by any theory, but it is believed that the compositions comprising MRM can mitigate the AD pathophysiology without having to directly act on brain, and thus allows for the reduction or un-wanted side effects. Drugs that must act in the brain to reduce neurodegeneration can induce un-wanted side effects. As AD drugs need to be administered continuously for decades, the reduction of unwanted side effects is important for long term compliance and use. The provided therapies targeting the gut and which remain in the gut such as MRM described herein may be able to avoid systemic and central side effects of brain targeted therapeutics to treat AD.

The present disclosure also contemplates kits for carrying out the methods described herein. The kits provided can contain the necessary components with which to carry out one or more of the above-noted methods. In one embodiment, the kit for treating a sleep wake disorder or a neurodegenerative disease is provided. The kit can comprise modified resistant maltodextrin or a composition comprising MRM and instructions for use including administration and dosaging information.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

EXAMPLES

Example 1: Making of Modified and Unmodified Resistant Maltodextrin

Figure 1B:
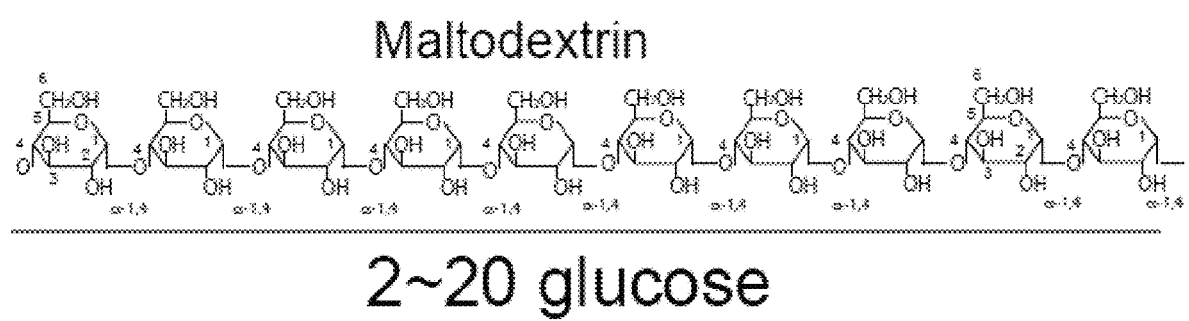
FIG. 1B depicts the structures of maltodextrin derived from amylase treatment of corn starch. Maltodextrin is produced by the digestion of non-heated cornstarch with amylase and glucoamylase.
Figure 1C:
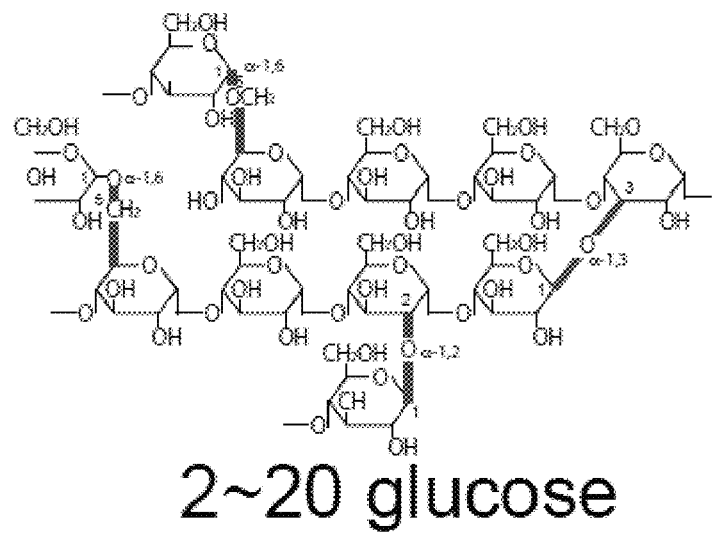
FIG. 1C depicts the structures of the unmodified resistant maltodextrin including multiple structures bonded at different positions. In order to produce resistant maltodextrin, corn starch is heated ~160° C. for 45 min followed by hydrolysis with amylase and glucoamylase. This heating process creates new glucosidic bonds such as alpha 1-2, 1-3, or 1-6 (shown in red), which is not cleaved by human enzyme. Red lines in resistant maltodextrin (RM) are chemical bonds highlighting the differences in chemical structures compared to maltodextrin (M) only digested with amylase and glucoamylase (no heat). This unmodified resistant maltodextrin is used in one embodiment to produce the MRM of the present invention.

Modified Resistant Maltodextrin (MRM) was prepared by preparing ~400 ml of 1% Resistant Maltodextrin (RM, www.fibersol.com/products/fibersol-2/) in water in regular mouse glass water bottle. Each water bottle was autoclaved at 120° C. for 20 minutes. The water bottles were left at room temperature overnight before use. FIG. 1C shows the starting material used, RM used in this process.

Unmodified Resistant Maltodextrin (RM) was prepared by first autoclaving 4 L of water at 120° C. for 20 minutes. The water is left overnight and then mixed with RM to make a 1% RM solution in the mouse water bottle. These water bottles were used in Example 2. The bottles were changed every week.

Example 2: Modified Resistant Maltodextrin can Improve Sleep-Wake Disorders

This Example shows a novel therapeutic to treat gut related disorders including sleep-wake disorders using derivatives of resistant maltodextrin (FIG. 1C) to modify gut microbiome to alter the gut-brain axis. Maltodextrin (M, FIG. 1B) is a product of cornstarch and is formed following amylase and glucoamylase digestion of starch. Maltodextrin itself has little effect on the gut microbiome. However, heating cornstarch and then treating with amylase and glucoamylase hydrolysis (17)(18), results in a highly cross linked form of maltodextrin which is referred to as resistant maltodextrin (RM) (FIG. 1C). Both RM and M are polymers of glucose and are of similar size (2-20 glucose monomers), but they differ in chemical linkages between monomers: RM contains $\alpha1$-2, $\alpha1$-3, $\alpha$ 1-4, and $\alpha$ 1-6 linkages, whereas the majority of glycosidic linkage in M is $\alpha1$-4 linkage (FIG. 1B,C). Of these, only the $\alpha1$-4 linkage is digestible by human enzymes, which is the reason RM is resistant to human digestion. Only gut microbes can break down the undigested glycosidic linkage of $\alpha$ 1-2, $\alpha$ 1-3, and $\alpha$ 1-6, and utilize glucose for fermentation.

RM treatment can cause gut microbiome remodeling. It is shown that RM treatment changes the gut microbiome in db/db mice, a commonly used model of type2 diabetes that develop glucose intolerance (1). Glucose metabolism was improved by RM treatment but also showed that the type of bacteria in the gastrointestinal tract was greatly modified as was the metabolome itself (1). Furthermore, when the microbiome of the RM treated mice is transplanted into naïve db/db mice, glucose homeostasis is improved, indicating that the altered gut microbiome is a cause for improvement of glucose metabolism in this model of type 2 diabetes.

T Modified resistant maltodextrin (MRM) or Unmodified resistant maltodextrin (RM) were given to db/db mice (genetically deficient in functional leptin receptor), via drinking water (1%). Sleep was monitored by continuous electroencephalographic (EEG) and electromyographic (EMG) recording. The mice used were ~8 weeks of age at the time of surgery and diet treatment was initiated ~10 weeks of age.

Figure 2:
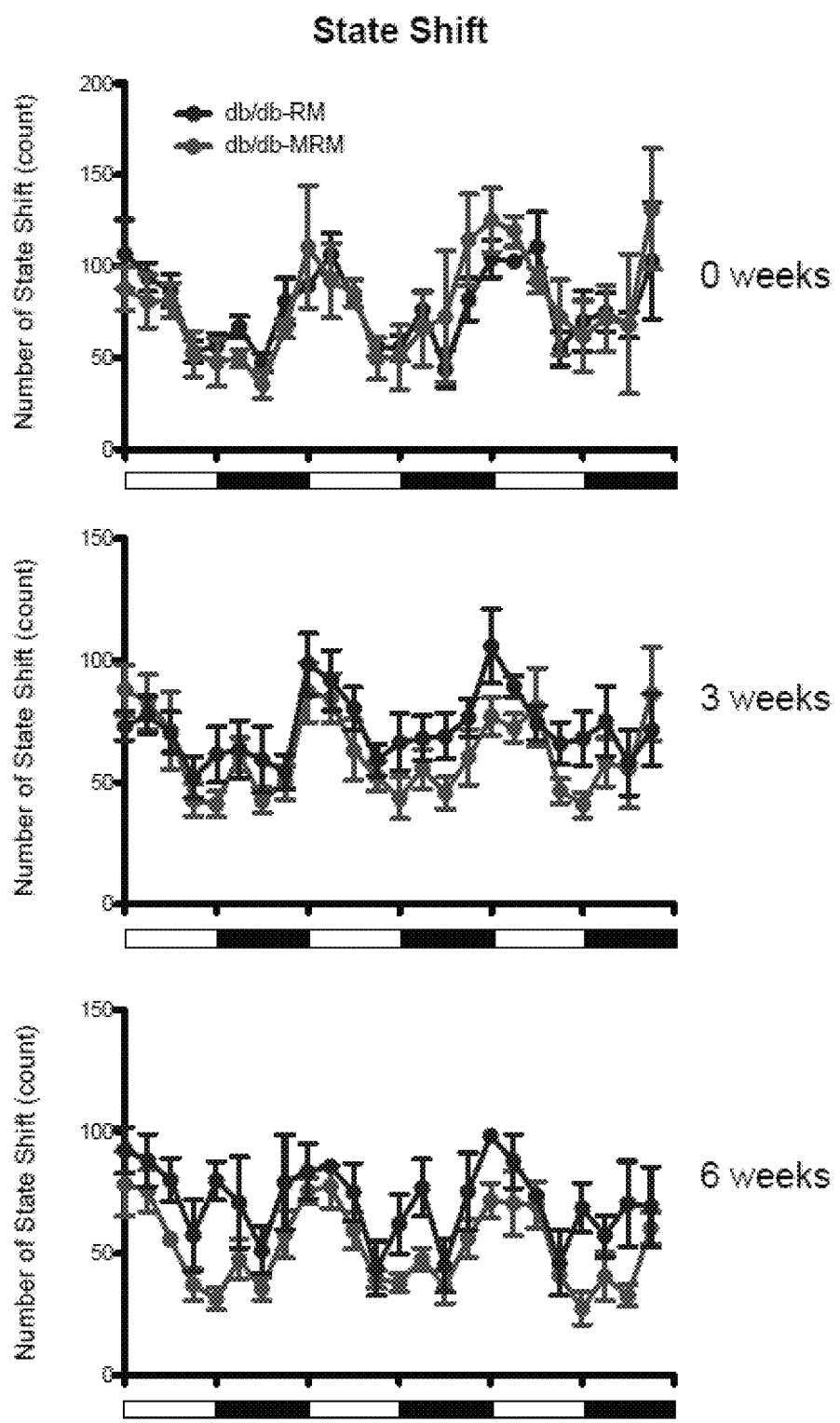
FIG. 2 depicts the number of state shifts in mice that were treated with the unmodified resistant maltodextrin (RM, blue) and modified resistant maltodextrin (MRM, red).
Figures 3A, 3B, 3C, 3D:
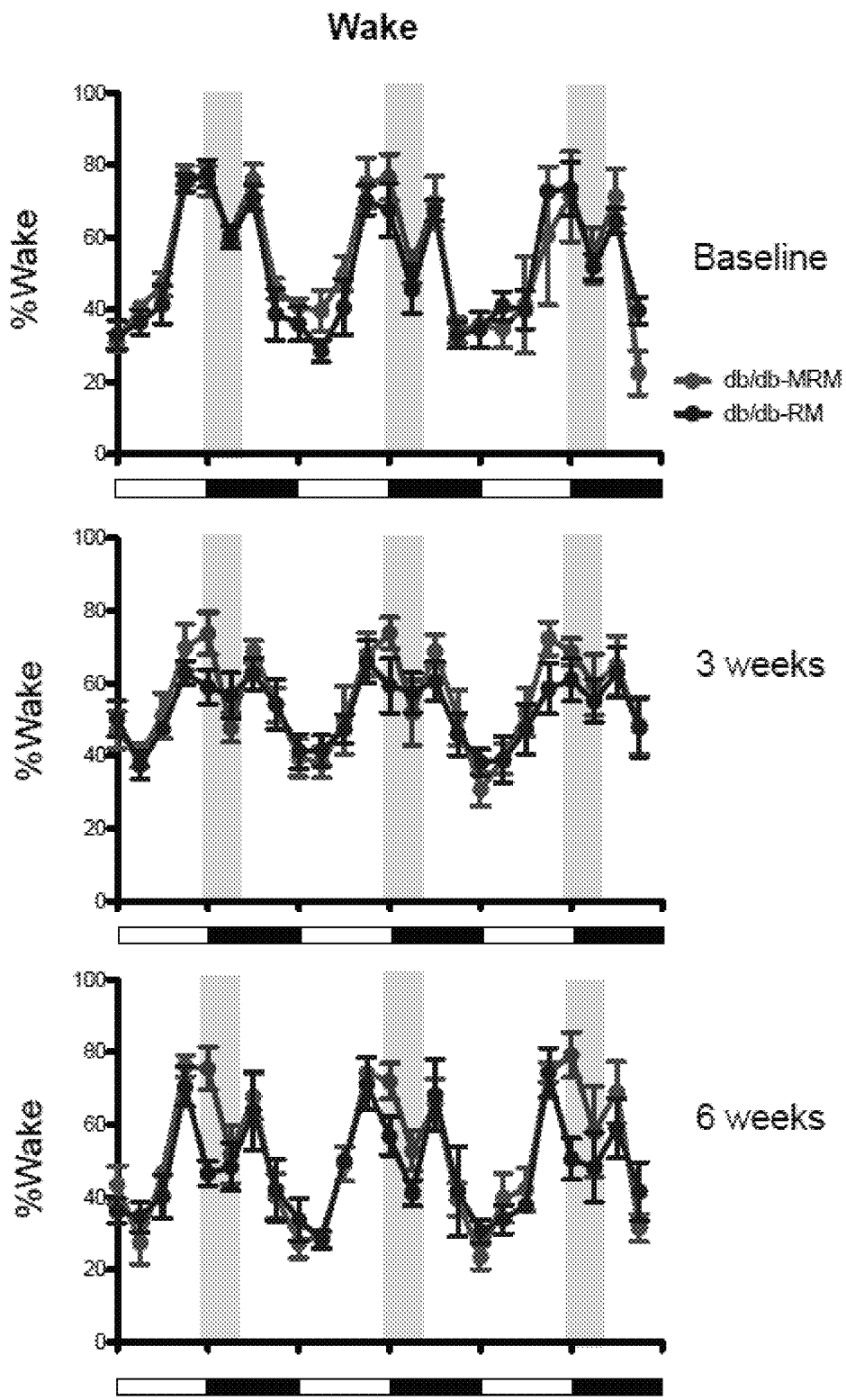
FIG. 3A-3D demonstrate the effect of RM or modified resistant maltodextrin (MRM) on mice sleep/wake cycle.
Figures 3A, 3B, 3C, 3D:
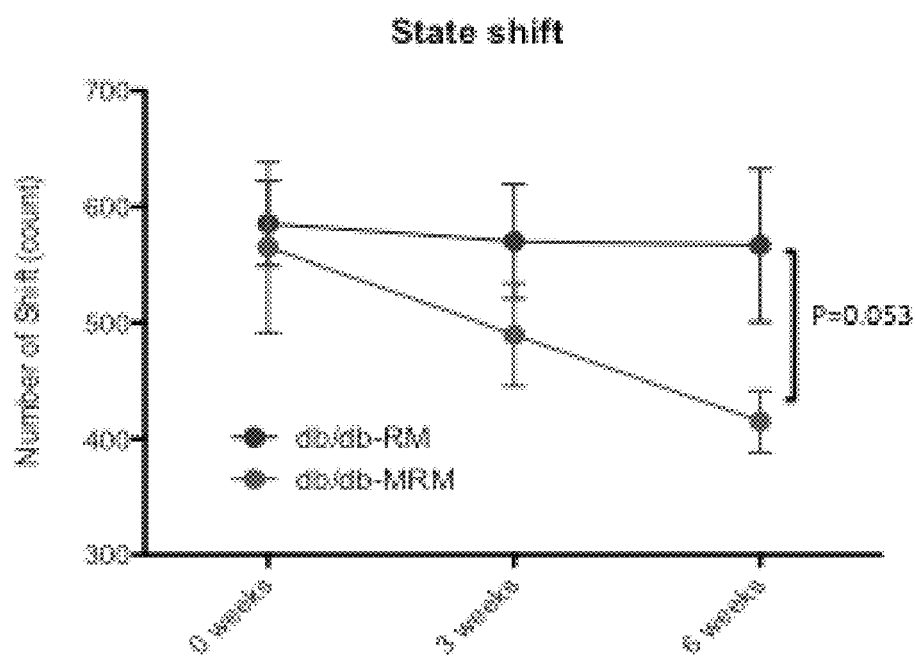

The db/db mutant mice have been widely used as a Type2 diabetic model and their sleep is significantly fragmented, analogous to what is observed in obese humans. Compared to wild-type mice, db/db mice exhibit higher numbers of state shift, with more sleep bouts, and decreased wake during the active phase. Mice drinking MRM showed significant mitigation of sleep fragmentation phenotypes including state shift (FIG. 2). In addition, the circadian amplitude of sleep-wake pattern was improved, as evidenced by increased wake during of the first 6 hours of the dark period (FIG. 3A bottom panel) and by increased temporal consolidation of REM (Rapid Eye Movement) sleep episodes (FIG. 3C).

The db/db mouse model has a compromised sleep-wake phenotype associated with its impaired glucose metabolism (11). Since connection between sleep and metabolism is well established, we tested if MRM may improve sleep-wake cycles in db/db after 6 weeks of treatment. Excessive nighttime sleep was significantly mitigated by MRM compared to RM (FIG. 3B). MRM also mitigated reduction of amplitude of circadian rhythm calculated by consolidation of phase of REM event (FIG. 3C). For sleep fragmentation, the effect of MRM was approaching to significant (p=0.053) and mice consume MRM tended to have lower sleep fragmentation (FIG. 3D).

Example 3: Modified Maltodextrin for Treatment of Alzheimer's Disease

A number of studies have shown that the gut microbiome of AD patients differs from normal individuals. Aβ expression and plaque formation is affected by the altered gut microbiota in AD animal models, and differences in the gut microbiota may produce an immune response and a proinflammatory state that may contribute to neurodegeneration and progression of AD (3-6). Recent studies revealed many novel and surprising functions that the gut microbiota play via the gut-brain axis (13, 14). Therefore, therapeutics that remodel the gut microbiota may be able to mitigate the AD pathophysiology without having to directly act on brain.

This is important because drugs that must act in the brain to reduce neurodegeneration can induce un-wanted side effects. This becomes a major problem for therapies that need to be administered continuously for decades as in the case of AD. The present therapies targeting the gut and which remain in the gut may be able to avoid systemic and central side effects of brain targeted therapeutics to treat AD.

We have employed a prebiotic approach to modify the gut microbiome to treat AD. This involves providing nutrients that are orally available such as undigestible carbohydrates to remodel the expression of specific types of microbes in the gut to produce desired effects on the host. We use undigestible carbohydrates in the form of dietary fiber because the fiber cannot be broken down by human digestive enzymes in the gut. As consequence it is transferred in the colon for intestinal bacteria to digest the glycosidic bonds to release glucose. This increases the quantity of available glucose for bacteria glycolysis needed for ATP production. Dietary fiber has been used for thousands of years and is generally safe in most humans.

Sleep and Memory Improvement in AD Mouse Model

To test whether MRM might be useful in treating AD, we tested the efficacy of MRM to reduce cognitive deficits and impaired sleep-wake function in the 5×FAD mouse model of AD (12). Previous studies by others have shown that these mice have altered gut-microbiome (6) as well as cognitive deficits and sleep/circadian rhythm disruption (19). We found that MRM was more effective than control (MM: Modified maltodextrin) in reducing excessive nighttime sleepiness (FIG. 4A) as well as improving of REM consolidation (FIG. 413) in this AD mouse. After 4 month of treatment (6 month of age) MRM was more effective than RM, MM or water in improving cognitive performance in the 24-hour memory of object location task, a form of spatial memory (FIG. 5A), in the 5×FAD mouse model (FIG. 513). Interestingly, MRM was also effective in improving cognitive function in wild-type littermate control mice (FIG. 5C). These studies show for the first time that our prebiotic therapy is effective in a mouse model of AD.

Deficient of Memory Consolidation is not Consequence of Learning Deficient

Figure 6:
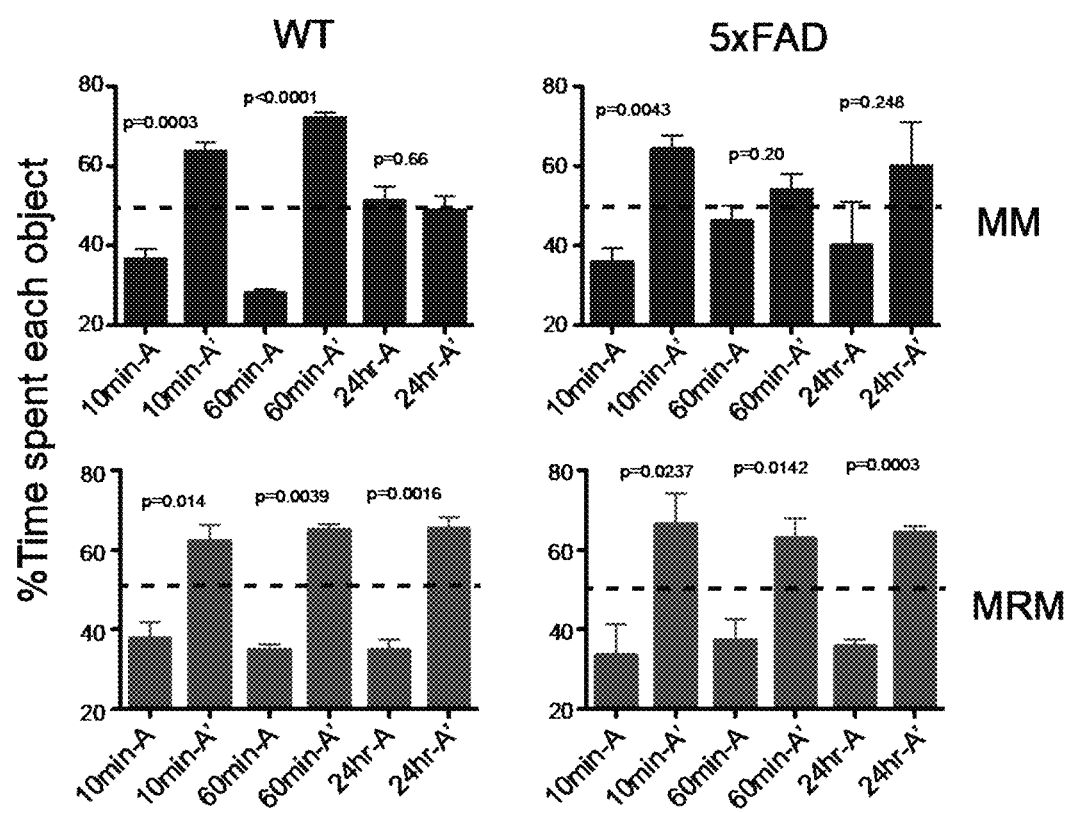
FIG. 6 demonstrates the effect of 4 months MRM and MM consumption on short term memory formation in 5×FAD and WT mice. Left two panels are from WT and right two are from 5×FAD. Top panels (blue) are mice consuming 1% MM and bottom panels are mice consuming 1% MRM. After 10 minutes of training, we detected short term memory formation in both treatments and genotypes.

In order to test if low memory consolidation seen in MM treated mice is consequence of learning deficient, we conducted object location memory test 10 min and 60 min after training. After 10 minutes of training, both MM and RM treated mice (6 months old) clearly formed special memory in both genotypes, suggesting that lack of special memory after 24 hours in MM is not result of lack of learning but lack of memory consolidation over 24 hours (FIG. 6). While MM treated 5×FAD mice lost special memory after 60 minutes of training, MM treated wild type kept their special memory up to 60 minutes.

Causal Role of Gut Microbiota in MRM Efficacy in Memory Consolidation

To directly address a causal role of gut microbial remodeling in mediating the beneficial effects of MRM in memory consolidation, we conducted fecal microbiota transplantation (FMT) experiments. Recipient mice (5×FAD or WT) were first treated with antibiotics cocktail to remove a vast majority of intrinsic gut bacteria. Subsequently, fecal suspensions from MRM treated donor mice (4 month treatment, 4 WT and 4 5×FAD) were pooled and administered to respective recipient mice via oral gavage. Object location memory test were conducted 2 and 4 months after FMT. After 2 month of FMT, only 5×FAD mice showed significant improvement of memory consolidation compared to control mice without FMT (FIG. 7 A,C). After 4 month of FMT, we observed memory improvement in both WT and 5×FAD and 5×FAD (FIG. 7 B,D). Of note, the recipient mice were never exposed to MRM indicating that gut microbiota in MRM donors were sufficient to confer the efficacy of MRM in memory consolidation after 24 hours in recipient mice.

Furthermore, as an AD therapeutic, it is designed to not only reduce cognitive decline but also improve sleep patterns, an earlier symptom not only of AD patients but also of elderly in general. Finally, our studies showed that MRM improved cognitive function not only in the AD mice but also in controls. This suggests that it may also be useful in treating decline in cognitive function in normal aging population.

Methods

Object Location Memory Test

Rodents have a natural tendency to approach and explore objects by touching and sniffing the objects. They have innate preferences for novelties such as objects and location.

This behavior can be easily quantified and utilized to assess rodent memory strength. Specifically, we allow mice to explore two identical objects for 5 minutes followed by a 10-minutes inter-trial. 24 hours later, we then moved one of the objects to a new location and allow animals to explore for 5 minutes. The percent of time explored for each object is quantified. This approach has many advantages compared to other memories tasks: requires less training time, animals experienced less stress due to calorie restriction (radial arm maze) or relatively cold water (Morris water maze).

Sleep Recording and Scoring

Mice will be surgically implanted with electrodes for electroencephalographic (EEG) recording and with bilateral nuchal muscle electrodes for electromyographic (EMG) recording. One week after surgery, sleep will be recorded for 72 hours. EEG/EMG data was analyzed and scored in 10-second epochs for sleep-wake states: Rapid Eye Movement sleep (REM), Non-REM sleep (NREM), and wake. We used a machine learning multiple classifier system to expedite sleep state scoring for mice (25). Fast Fourier analysis is used to quantify EEG power bands for distinct vigilance states, such as slow-wave (delta) power during NREM sleep. Custom software is used to calculate 52 distinct parameters of sleep from scored data, which factor analysis (26) has indicated measure five different dimensions of sleep-wake behavior: (1) sleep amounts, (2) REM sleep, (3) sleep fragmentation, (4) EEG power bands, and (5) circadian timing of sleep.

Fecal Microbiota Transplantation (FMT)

Recipient mice are treated with a cocktail of broad spectrum antibiotics (1 g/L ampicillin, neomycin, and metronidazole and 0.5 g/L vancomycin) in drinking water for 1 weeks. The mice were allowed 3-4 days to recover before fecal microbiota transplantation started. Fresh fecal pellets were collected from donor mice. Subsequently, 200 mg of pellets were weighed and resuspended and homogenzied at 1:10 (w/v) in transfer buffer (0.1 M phosphate buffered saline, pH 7.0, pre-reduced with 0.05% cysteine HCl). To each recipient mouse, 100 µl of homogenates were used for oral gavage. The transplantation procedure was carried out every three days, four times total for each experiment. Throughout the entire experimental period, the mice were maintained on the regular chow diet. Recipient mice never exposed to MRM. Object location memory test was conducted 2 month and 4 month after FMT.

REFERENCES CITED

1. He B, Nohara K, Ajami N J, Michalek R D, Tian X, Wong M, Losee-Olson S H, Petrosino J F, Yoo S H, Shimomura K, Chen Z. Transmissible microbial and metabolomic remodeling by soluble dietary fiber improves metabolic homeostasis. Sci Rep. 2015; 5:10604. doi: 10.1038/srep10604. PubMed PMID: 26040234; PMCID: PMC4455235.
2. Cummings J. Lessons Learned from Alzheimer Disease: Clinical Trials with Negative Outcomes. Clin Transl Sci. 2018; 11(2):147-52. Epub 2017/08/03. doi: 10.1111/cts.12491. PubMed PMID: 28767185; PMCID: PMC5866992.
3. Vogt N M, Kerby R L, Dill-McFarland K A, Harding S J, Merluzzi A P, Johnson S C, Carlsson C M, Asthana S, Zetterberg H, Blennow K, Bendlin B B, Rey F E. Gut microbiome alterations in Alzheimer's disease. Sci Rep. 2017; 7(1):13537. Epub 2017/10/21. doi: 10.1038/s41598-017-13601-y. PubMed PMID: 29051531; PMCID: PMC5648830.
4. Sochocka M, Donskow-Lysoniewska K, Diniz B S, Kurpas D, Brzozowska E, Leszek J. The Gut Microbiome Alterations and Inflammation-Driven Pathogenesis of Alzheimer's Disease-a Critical Review. Mol Neurobiol. 2018. Epub 2018/06/25. doi: 10.1007/s12035-018-1188-4. PubMed PMID: 29936690.
5. Minter M R, Zhang C, Leone V, Ringus D L, Zhang X, Oyler-Castrillo P, Musch M W, Liao F, Ward J F, Holtzman D M, Chang E B, Tanzi R E, Sisodia S S. Antibiotic-induced perturbations in gut microbial diversity influences neuro-inflammation and amyloidosis in a murine model of Alzheimer's disease. Sci Rep. 2016; 6:30028. Epub 2016/07/23. doi: 10.1038/srep30028. PubMed PMID: 27443609; PMCID: PMC4956742.
6. Brandscheid C, Schuck F, Reinhardt S, Schafer K H, Pietrzik C U, Grimm M, Hartmann T, Schwiertz A, Endres K. Altered Gut Microbiome Composition and Tryptic Activity of the 5×FAD Alzheimer's Mouse Model. J Alzheimers Dis. 2017; 56(2):775-88. Epub 2016/12/31. doi: 10.3233/JAD-160926. PubMed PMID: 28035935.
7. So E Y, Ouchi M, Cuesta-Sancho S, Olson S L, Reif D, Shimomura K, Ouchi T. Tumor suppression by resistant maltodextrin, Fibersol-2. Cancer Biol Ther. 2015; 16(3): 460-5. Epub 2015/02/19. doi: 10.1080/15384047.2015.1009269. PubMed PMID: 25692338; PMCID: PMC4622535.
8. Sancho S C, Olson S L, Young So E, Shimomura K, Ouchi T, Preuss F. Fibersol-2 induces apoptosis of Apc-deficient colorectal Cancer (SW480) cells and decreases polyp formation in Apc MIN mice. Cancer Biol Ther. 2016; 17(6):657-63. Epub 2016/05/05. doi: 10.1080/15384047.2016.1177685. PubMed PMID: 27143108; PMCID: PMC4990394.
9. Hashizume C, Kishimoto Y, Kanahori S, Yamamoto T, Okuma K, Yamamoto K. Improvement effect of resistant maltodextrin in humans with metabolic syndrome by continuous administration. J Nutr Sci Vitaminol (Tokyo). 2012; 58(6):423-30. PubMed PMID: 23419401.
10. Hashizume C, Okuma K. Fiber Ingredients: Food Application and Health Benefits. CRC press. 2009:pp. 61-78.
11. Laposky A D, Bradley M A, Williams D L, Bass J, Turek F W. Sleep-wake regulation is altered in leptin-resistant (db/db) genetically obese and diabetic mice. Am J Physiol Regul Integr Comp Physiol. 2008; 295(6):R2059-66. doi: 10.1152/ajpregu.00026.2008. PubMed PMID: 18843095; PMCID: PMC2685290.
12. Oakley H, Cole S L, Logan S, Maus E, Shao P, Craft J, Guillozet-Bongaarts A, Ohno M, Disterhoft J, Van Eldik L, Berry R, Vassar R. Intraneuronal beta-amyloid aggregates, neurodegeneration, and neuron loss in transgenic mice with five familial Alzheimer's disease mutations: potential factors in amyloid plaque formation. J Neurosci. 2006; 26(40):10129-40. Epub 2006/10/06. doi: 10.1523/JNEUROSCI.1202-06.2006. PubMed PMID: 17021169.
13. Maqsood R, Stone T W. The Gut-Brain Axis, BDNF, NMDA and CNS Disorders. Neurochem Res. 2016; 41(11):2819-35. doi: 10.1007/s11064-016-2039-1. PubMed PMID: 27553784.
14. Saulnier D M, Ringel Y, Heyman M B, Foster J A, Bercik P, Shulman R J, Versalovic J, Verdu E F, Dinan T G, Hecht G, Guarner F. The intestinal microbiome, probiotics and prebiotics in neurogastroenterology. Gut Microbes. 2013; 4(1):17-27. Epub 2012/12/04. doi: 10.4161/gmic.22973. PubMed PMID: 23202796; PMCID: PMC3555881.
15. Akbari E, Asemi Z, Daneshvar Kakhaki R, Bahmani F, Kouchaki E, Tamtaji O R, Hamidi G A, Salami M. Effect of Probiotic Supplementation on Cognitive Function and Metabolic Status in Alzheimer's Disease: A Randomized, Double-Blind and Controlled Trial. Front Aging Neurosci. 2016; 8:256. Epub 2016/11/29. doi: 10.3389/fnagi.2016.00256. PubMed PMID: 27891089; PMCID: PMC5105117.
16. Liberti M V, Locasale J W. The Warburg Effect: How Does it Benefit Cancer Cells? Trends Biochem Sci. 2016; 41(3):211-8. Epub 2016/01/19. doi: 10.1016/j.tibs.2015.12.001. PubMed PMID: 26778478; PMCID: PMC4783224.
17. Baer D J, Stote K S, Henderson T, Paul D R, Okuma K, Tagami H, Kanahori S, Gordon D T, Rumpler W V, Ukhanova M, Culpepper T, Wang X, Mai V. The metabolizable energy of dietary resistant maltodextrin is variable and alters fecal microbiota composition in adult men. J Nutr. 2014; 144(7):1023-9. doi: 10.3945/jn.113.185298. PubMed PMID: 24744316.
18. Fastinger N D, Karr-Lilienthal L K, Spears J K, Swanson K S, Zinn K E, Nava G M, Ohkuma K, Kanahori S, Gordon D T, Fahey G C, Jr. A novel resistant maltodextrin alters gastrointestinal tolerance factors, fecal characteristics, and fecal microbiota in healthy adult humans. J Am Coll Nutr. 2008; 27(2):356-66. PubMed PMID: 18689571.
19. Sethi M, Joshi S S, Webb R L, Beckett T L, Donohue K D, Murphy M P, O'Hara B F, Duncan M J. Increased fragmentation of sleep-wake cycles in the 5xFAD mouse model of Alzheimer's disease. Neuroscience. 2015; 290: 80-9. Epub 2015/02/01. doi: 10.1016/j.neuroscience.2015.01.035. PubMed PMID: 25637807; PMCID: PMC4361816.
20. Djonlagic I, Saboisky J, Carusona A, Stickgold R, Malhotra A. Increased sleep fragmentation leads to impaired off-line consolidation of motor memories in humans. PLoS One. 2012; 7(3):e34106. doi: 10.1371/journal.pone.0034106. PubMed PMID: 22470524; PMCID: PMC3314699.
21. Lim A S, Kowgier M, Yu L, Buchman A S, Bennett D A. Sleep Fragmentation and the Risk of Incident Alzheimer's Disease and Cognitive Decline in Older Persons. Sleep. 2013; 36(7):1027-32. doi: 10.5665/sleep.2802. PubMed PMID: 23814339; PMCID: PMC3669060.
22. Sprecher K E, Koscik R L, Carlsson C M, Zetterberg H, Blennow K, Okonkwo O C, Sager M A, Asthana S, Johnson S C, Benca R M, Bendlin B B. Poor sleep is associated with CSF biomarkers of amyloid pathology in cognitively normal adults. Neurology. 2017; 89(5):445-53. doi: 10.1212/WNL.0000000000004171. PubMed PMID: 28679595; PMCID: PMC5539733.
23. Walsh C M, Blackwell T, Tranah G J, Stone K L, Ancoli-Israel S, Redline S, Paudel M, Kramer J H, Yaffe K. Weaker circadian activity rhythms are associated with poorer executive function in older women. Sleep. 2014; 37(12):2009-16. doi: 10.5665/sleep.4260. PubMed PMID: 25337947.
24. Tranah G J, Blackwell T, Stone K L, Ancoli-Israel S, Paudel M L, Ensrud K E, Cauley J A, Redline S, Hillier T A, Cummings S R, Yaffe K. Circadian activity rhythms and risk of incident dementia and mild cognitive impairment in older women. Ann Neurol. 2011; 70(5):722-32. Epub 2011/12/14. doi: 10.1002/ana.22468. PubMed PMID: 22162057; PMCID: PMC3244839.
25. Gao V, Turek F, Vitaterna M. Multiple classifier systems for automatic sleep scoring in mice. J Neurosci Methods. 2016; 264:33-9. Epub 2016/03/02. doi: 10.1016/j.jneumeth.2016.02.016. PubMed PMID: 26928255; PMCID: PMC4833589.
26. Winrow C J, Williams D L, Kasarskis A, Millstein J, Laposky A D, Yang H S, Mrazek K, Zhou L, Owens J R, Radzicki D, Preuss F, Schadt E E, Shimomura K, Vitaterna M H, Zhang C, Koblan K S, Renger J J, Turek F W. Uncovering the genetic landscape for multiple sleep-wake traits. PLoS One. 2009; 4(4):e5161. Epub 2009/04/11. doi: 10.1371/journal.pone.0005161. PubMed PMID: 19360106; PMCID: PMC2664962.

Each publication, patent, and patent publication cited in this disclosure is incorporated in reference herein in its entirety. The present invention is not intended to be limited to the foregoing examples, but encompasses all such modifications and variations as come within the scope of the appended claims.

The invention claimed is:

1. A method of improving memory in a subject who has been diagnosed with or having Alzheimer's disease, the method comprising (i) providing a modified resistant maltodextrin by heating resistant maltodextrin in water at a temperature from about 95° C. to 160° C. for about 20 minutes to about overnight, and (ii) administering an effective amount of the modified resistant maltodextrin in (i) to the subject to improve memory in the subject.

2. The method of claim 1, wherein the memory is spatial memory.

3. The method of claim 1, wherein the modified resistant maltodextrin is administered in an amount of about 30 g/day.

4. A method of treating a sleep-wake disorder in a subject having Alzheimer's disease, Parkinson's disease, or multiple sclerosis, the method comprising i) providing a modified resistant maltodextrin by heating resistant maltodextrin in water at a temperature from about 95° C. to 160° C. for about 20 minutes to about overnight, and (ii) administering an effective amount of the modified resistant maltodextrin in (i) to the subject to treat the sleep-wake disorder in the subject.

5. A method of improving memory in a subject, the method comprising (i) providing a modified resistant maltodextrin by heating resistant maltodextrin in water at a temperature from about 95° C. to 160° C. for about 20 minutes to about overnight, and (ii) administering an effective amount of the modified resistant maltodextrin in (i) to improve memory in the subject.

6. The method of claim 5, wherein the memory is spatial memory.

7. The method of claim 5, wherein the subject does not have a neurodegenerative disease.

8. The method of claim 5, wherein the subject has Parkinson's disease or multiple sclerosis.

9. The method of claim 8, wherein the memory is spatial memory.

* * * * *